(12) United States Patent
Masui et al.

(10) Patent No.: US 8,575,189 B2
(45) Date of Patent: Nov. 5, 2013

(54) TACROLIMUS PREPARATION FOR EXTERNAL APPLICATIONS

(75) Inventors: Hironori Masui, Saitama (JP); Shimpei Sato, Saitama (JP)

(73) Assignee: Takata Seiyaku Co., Ltd., Tokyo (JP)

( * ) Notice: Subject to any disclaimer, the term of this patent is extended or adjusted under 35 U.S.C. 154(b) by 215 days.

(21) Appl. No.: 13/122,820

(22) PCT Filed: Oct. 7, 2009

(86) PCT No.: PCT/JP2009/067488
§ 371 (c)(1),
(2), (4) Date: Apr. 6, 2011

(87) PCT Pub. No.: WO2010/041684
PCT Pub. Date: Apr. 15, 2010

(65) Prior Publication Data
US 2011/0212988 A1    Sep. 1, 2011

(30) Foreign Application Priority Data
Oct. 8, 2008   (JP) ................................. 2008-261987

(51) Int. Cl.
*A61K 31/44* (2006.01)
(52) U.S. Cl.
USPC ........................................................ 514/291
(58) Field of Classification Search
USPC ........................................................ 514/291
See application file for complete search history.

(56) References Cited

U.S. PATENT DOCUMENTS

| | | | |
|---|---|---|---|
| 4,894,366 A | 1/1990 | Okuhara et al. | |
| 4,929,611 A | 5/1990 | Okuhara et al. | |
| 4,956,352 A | 9/1990 | Okuhara et al. | |
| 5,110,811 A | 5/1992 | Okuhara et al. | |
| 5,254,562 A | 10/1993 | Okuhara et al. | |
| 5,266,692 A | 11/1993 | Okuhara et al. | |
| 5,366,971 A | 11/1994 | Grassberger et al. | |
| 5,385,907 A | 1/1995 | Asakura et al. | |
| 5,496,727 A | 3/1996 | Okuhara et al. | |
| 5,565,559 A | 10/1996 | Okuhara et al. | |
| 5,624,842 A | 4/1997 | Okuhara et al. | |
| 5,665,727 A | 9/1997 | Grassberger et al. | |
| 5,830,717 A | 11/1998 | Okuhara et al. | |
| 5,939,427 A | 8/1999 | Kagayama et al. | |
| 6,028,097 A | 2/2000 | Okuhara et al. | |
| 6,201,005 B1 | 3/2001 | Okuhara et al. | |
| 6,387,918 B1 | 5/2002 | Yamanaka et al. | |
| 6,482,845 B1 | 11/2002 | Okuhara et al. | |
| 6,586,444 B2 | 7/2003 | Ibuki et al. | |
| 6,673,808 B1 | 1/2004 | Ibuki et al. | |
| 2002/0032212 A1 | 3/2002 | Yamanaka et al. | |
| 2003/0170831 A1 | 9/2003 | Okuhara et al. | |
| 2003/0229115 A1 | 12/2003 | Okuhara et al. | |
| 2004/0029908 A1 | 2/2004 | Okuhara et al. | |
| 2005/0059694 A1 | 3/2005 | Grassberger et al. | |
| 2005/0124646 A1 | 6/2005 | Okuhara et al. | |
| 2006/0115522 A1 | 6/2006 | Lulla et al. | |
| 2007/0190080 A1 | 8/2007 | Friedman | |
| 2007/0196459 A1* | 8/2007 | Zhang et al. .................. 424/448 |
| 2007/0287688 A1* | 12/2007 | Chan et al. .................... 514/169 |
| 2008/0050434 A1* | 2/2008 | Jain et al. ...................... 424/485 |

FOREIGN PATENT DOCUMENTS

| | | |
|---|---|---|
| EP | 0 474 126 | 3/1992 |
| EP | 1 074 255 | 2/2001 |
| JP | 61-148181 | 7/1986 |
| JP | 63-255227 | 10/1988 |
| JP | 1-157913 | 6/1989 |
| JP | 5-17481 | 1/1993 |
| JP | 6-256182 | 9/1994 |
| JP | 7-196515 | 8/1995 |
| JP | 7-291868 | 11/1996 |
| JP | 2000-513739 | 10/2000 |
| JP | 2007-517859 | 7/2007 |
| WO | 94/28894 | 12/1994 |
| WO | 99/55332 | 11/1999 |
| WO | 00/50007 | 8/2000 |
| WO | 2004/071510 | 8/2004 |
| WO | 2005/065652 | 7/2005 |
| WO | 2005/087195 | 9/2005 |
| WO | 2006/062334 | 6/2006 |
| WO | 2007/100376 | 9/2007 |

OTHER PUBLICATIONS

International Search Report issued Nov. 17, 2009 in International (PCT) Application No. PCT/JP2009/067488.
Chakkapan et al., "Studies in Transdermal Drug Delivery Systems for Estradiol", Indian J. Pharm. Sci., vol. 56, No. 4, 1994, pp. 121-125.
Fiume, "Final Report on the Safety Assessment of Triacetin" Int. J. Toxicol., vol. 22, Suppl. 2, 2003, pp. 1-10.
Japanese Office Action issued Jun. 5, 2012 in corresponding Japanese Patent Application No. 2010-532940, with English language translation.
Package insert, Therapeutic agent for atopic dermatitis, PROTOPIC® Ointment 0.1%, Tacrolimus monohydrate ointment, approved Jun. 1999, revised Aug. 2008, 10th edition, with partial English translation.
Material Safety Data Sheet, "Propylene Carbonate", Toxicity Information, Nacalai Tesque, Inc., published on Sep. 20, 1994, with partial English translation.

(Continued)

*Primary Examiner* — Rei-tsang Shiao
(74) *Attorney, Agent, or Firm* — Wenderoth, Lind & Ponack, L.L.P.

(57) ABSTRACT

The present invention provides tacrolimus containing ointment having low dermal irritation and excellent stability. It was found that an ointment comprising triacetin as a solubilizer for tacrolimus may sufficiently solubilize tacrolimus, has low dermal irritation and excellent stability. Preferably, the ointment of the present invention is an o/o type (oil-in-oil type) ointment in which tacrolimus-solubilized triacetin droplets are dispersed in an ointment base, preferably a mixture of beeswax and petrolatum.

9 Claims, No Drawings

(56) References Cited

OTHER PUBLICATIONS

Japanese Pharmaceutical Excipients Directory 2007, edited by Japan Pharmaceutical Excipients Council, issued by Yakuji Nippo, Ltd., Jul. 25, 2007, "Propylene Carbonate" and "Triacetin", pp. 173 and 192-193, with partial English translation.
Material Safety Data Sheet, "Triacetin", Toxicity Information, Yuki Gosei Kogyo Co., Ltd., revised on Nov. 30, 2007, with partial English translation.
Supplemental European Search Report issued Jan. 25, 2012 in corresponding European Application No. 09 81 9218.
International Preliminary Report on Patentability issued Jun. 16, 2011 in International (PCT) Application No. PCT/JP2009/067488.
V. Borhade et al., "Design and Evaluation of Self-Microemulsifying Drug Delivery System (SMEDDS) of Tacrolimus", AAPS PharmSciTech, vol. 9, No. 1, 2008, pp. 13-21.
G. Buech et al., "Formulation of Sirolimus Eye Drops and Corneal Permeation Studies", Journal of Ocular Pharmacology and Therapeutics, vol. 23, No. 3, 2007, pp. 292-303.
Pharmaceutical Interview Form, Protopic Ointment 0.1%, Revised $7^{th}$ Edition, Apr. 2005, pp. 6-7, with English translation.

* cited by examiner

TACROLIMUS PREPARATION FOR EXTERNAL APPLICATIONS

FIELD OF THE INVENTION

The present invention relates to an external preparation comprising tacrolimus as an active ingredient. In particular, the present invention relates to a tacrolimus containing external preparation having low dermal irritation upon applying to a subject and excellent stability.

BACKGROUND OF THE INVENTION

Tacrolimus, a member of macrolides immunosuppressant, chemical name 17-aryl-1,14-dihydroxy-12-[2-(4-hydroxy-3-methoxycyclohexyl)-1-methylbinyl]-23,25-dimethoxy-13,19,21,27-tetramethyl-11,28-dioxa-4-azatricyclo [22.3.1.04,9] octacos-18-en-2,3,10,16-tetraone has been isolated from culture of Streptomyces tsukubaensis, and its monohydrate form represented by the following formula:

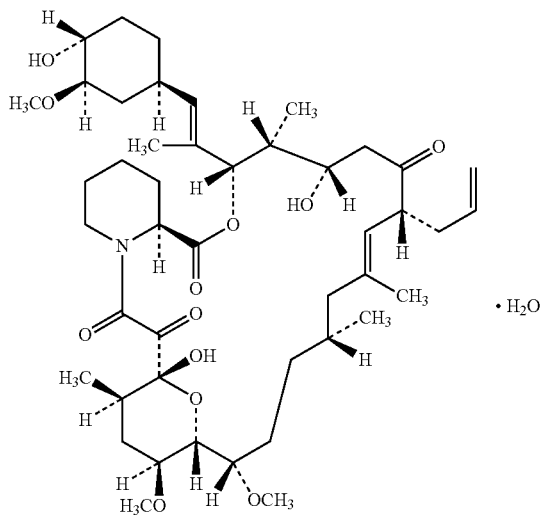

has been commonly used as a pharmaceutical. It has been known that tacrolimus has advantageous pharmacological effects including immunosuppressant effect and antimicrobial effect, and that it is thus useful for the treatment and prevention of various autoimmune diseases such as organ or tissue transplant rejection or graft vs host disease, infection diseases and the like (see Patent Reference 1).

It has also been known that external application of tacrolimus is useful for the treatment of cutaneous diseases such as atopic dermatitis (Patent Reference 2). There has been a significant increase in the number of patients suffering from atopic dermatitis recently. It has been known that skin of a patient suffering from atopic dermatitis has lower contents of epidermal lipid and keratoid moisture, lesser ability to form hydrolipidic film, and lower resistance threshold against external irritations comparing to those of normal subjects. Furthermore, it has also been known that abnormal-dryness or pruritus of skin results from a wreck of barrier function of skin. Therefore, there is a need for an external preparation comprising tacrolimus.

Since tacrolimus dissolves poorly in water and lipid solvent, a preparation comprising it requires solubilizers capable of solubilizing tacrolimus. Typically surfactants are used as the solubilizer. However, surfactants are not suitable for a preparation for treating cutaneous diseases such as atopic dermatitis because of its dermal irritation. Useful solubilizers other than surfactants are very limited. Such solubilizers may have dermal irritation like as surfactants or may chemically destabilize an active ingredient such as tacrolimus, it is thus unfavorable to use solubilizers having said undesired properties. In addition, for the purpose of decreasing dermal irritation caused by tacrolimus ointment, preferred is solubilizers capable of forming stable droplet dispersion which do not misce with ointment base. Moreover, in the case of the treatment of cutaneous diseases such as atopic dermatitis, preferred is topical delivery of tacrolimus because the drug is an immunosuppressant. If tacrolimus is administered systemically, undesired side effects such as dysfunction of kidney and a risk to be affected with diseases which must be normally prevented by an immune system would be caused. Furthermore, preferred is having sufficient chemical and physical stability for a pharmaceutical product.

There has been tacrolimus containing external preparations, for example ointment (see Patent Reference 3), lotion (see Patent Reference 4), cream (see Patent Reference 5) and gel (see Patent Reference 6). However there are technical problems in those preparations that the preparation comprises agents having high dermal irritation or that the active ingredient tacrolimus is decomposed during long-term storage. Therefore, there is still a need for a tacrolimus containing external preparation having low dermal irritation and excellent stability. For example, there has been marketed a tacrolimus ointment as the trade name Protopic® ointment, which comprises propylene carbonate. However propylene carbonate has dermal irritation, it is thus not suitable for na ointment.

Patent Reference 1: JP-A-61-148181
Patent Reference 2: JP-A-1-157913
Patent Reference 3: JP-A-5-17481
Patent Reference 4: WO94/028894
Patent Reference 5: JP-A-2000-513739
Patent Reference 6: WO99/055332

SUMMARY OF THE INVENTION

Technical Problems to be Solved by the Invention

Accordingly, the purpose of the present invention is to provide a tacrolimus containing external preparation having low dermal irritation and excellent stability.

Means to Solve the Problems

We now found that an external preparation comprising triacetin as a solubilizer of tacrolimus has low dermal irritation and excellent stability. Accordingly, the present invention provides an external preparation comprising tacrolimus as an active ingredient and triacetin as a solubilizer therefor.

Effect of the Invention

The external preparation of the present invention not only has low dermal irritation and excellent stability, but also forms stable droplet of tacrolimus-solubilized triacetin because a base does not misce with triacetin. Such external preparation may topically deliver tacrolimus to a subject.

DETAILED DESCRIPTION OF THE PREFERRED EMBODIMENTS

In the first embodiment, the present invention provides an external preparation comprising tacrolimus, triacetin and a base. Preferably, the percentage of the amount of tacrolimus to triacetin may be from 0.03 to 30% by weight, more preferably from 0.2 to 12.5% by weight, most preferably from 0.5 to 3.3% by weight.

The term "Tacrolimus", as used herein, means 23-membered macrolide system lactone as described above, which is also known as FK-506 or Fujimycin. Tacrolimus may be a free or pharmaceutically acceptable salt form, or a solvate such as hydrate or analog thereof. Since a salt form, a solvate or an analog of tacrolimus, especially tacrolimus monohydrate has a similar pharmacological activity to tacrolimus in a free form, the term "tacrolimus", as used in the present application and claims, means any or all of them. The term "tacrolimus" also includes tacrolimus in crystalline phase, non-crystalline phase or semicrystalline phase. Preferably, the external preparation of the present invention comprises tacrolimus at 0.01 to 1.0% by weight, more preferably 0.02 to 0.5% by weight, most preferably 0.03 to 0.1% by weight for the total amount of the preparation.

The term "triacetin", as used herein, means compound represented by the following formula:

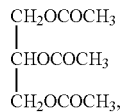

(chemical name: glycerin triacetate). The properties of triacetin are described in Iyakuhin Tenkabutsu Kikaku 2003 and Iyakuhin Tenkabutsu Jiten 2007 (Yakuji Nippo), which are incorporated herein by reference. Tacrolimus in a free form may dissolve in triacetin at 25° C. in the ratio of about 12.5 g/100 g. Preferably, the external preparation of the present invention comprises triacetin at 0.1 to 30% by weight, more preferably 1.0 to 20% by weight, still more preferably 3.0 to 6.0% by weight, most preferably 4.0 to 5.0% by weight for the total amount of the preparation.

The term "external preparation", as used herein, means a preparation for applying to skin or mucosa of a subject, for example skin, eye, nasal cavity, ear, anus, vagina, urethra, intraanus, trachea, lung, sublingual, oral cavity or the like, typically including ointment, liquid, lotion, liniment, gel, aerosol, plaster, cataplasm or cream. In a preferred embodiment of the present invention, the term "external preparation" means ointments or ophthalmic ointments as defined in Japanese Pharmacopoeia Fifteenth Edition, General Rules for Preparations, which is incorporated herein by reference.

More preferably, the ointment of the present invention may be an oleaginous ointment. The term "oleaginous ointment", as used herein, means any ointments in which an active ingredient is dispersed and/or dissolved in an oleaginous base, or a solution of an active ingredient is dispersed in an oleaginous base, except for ointments substantially comprising emulsion base, water soluble base or lotion base. In more preferable embodiment, the ointment of the present invention is an ointment in an oil-in-oil type emulsion form in which tacrolimus-solubilizing triacetin droplets are dispersed in a base.

The term "emulsion", as used herein, means a liquid mixture in which fine droplets are dispersed or suspended in other liquid incapable of miscing with the droplets. Emulsion, as used herein, also contains microemulsion, in which smaller droplets are dispersed. Though the droplet and liquid is typically either water or oil, those may be oil and oil as long as they substantially do not dissolve each other. Typically, the volume average particle size of the emulsion droplets ranges preferably from about 0.01 μm to 500 μm, more preferably from 0.1 μm to 50 μm as measured by for example laser diffractometry.

The external preparation of the present invention comprises a base, in addition to tacrolimus as an active ingredient and triacetin as a solubilizer of tacrolimus. The base may be any one of the base or a mixture of bases suitable for an external preparation. The base normally exerts no medicinal effect by itself. Examples of the base include for example oily base or hydrophobic base, emulsion base, hydrophilic base or water-soluble base, gel base, or conventional components such as fatty acids or derivatives thereof, ester of polycarboxylic acid and alcohol, higher alcohol, powdery inorganic materials, gel forming agent, water, alcohol, polyol, alkanolamine, propellant or the like. The base actually used in a certain preparation may vary depending on the formulation, while the base can be easily selected by a person skilled in the art field on the basis of well known factors including a desired preparation, titer of an active ingredient, desired release rate of an active ingredient and the like.

In more particular embodiment, the base includes, but not limited to, for example water, animals and plants oil (e.g. olive oil, corn oil, peanut oil, sesame oil, caster oil or the like), lower alcohol (e.g. ethanol, propanol, propyleneglycol, 1,3-butyleneglycol, phenol or the like), higher fatty acid and ester thereof, wax, higher alcohol, polyol, hydrophilic petrolatum, purified lanolin, absorptive ointment, hydrous lanolin, hydrophilic ointment, starch, pullulan, gum arabic, tragacanth gum, gelatin, dextran, cellulose derivatives (e.g. methyl cellulose, carboxymethyl cellulose, hydroxyethyl cellulose, hydroxypropylcellulose or the like), synthetic polymers (e.g. carboxy vinyl polymer, sodium polyacrylate, polyvinyl alcohol, polyvinyl pyrrolidone or the like), propylene glycol, macrogol (e.g. macrogol 200 to 600 or the like) and combination thereon.

In particular, the base of an ointment includes higher fatty acid and ester thereof (e.g. adipic acid, myristic acid, palmitic acid, stearic acid, oleic acid, adipate ester, myristate ester, palmitate ester, diethyl sebacate, hexyl laurate, cetyl isooctanoate, lanolin and lanolin derivatives), wax (e.g. whale wax, beeswax, ceresin), higher alcohol (e.g. cetanol, stearyl alcohol, cetostearyl alcohol), hydrocarbons (e.g. hydrophilic petrolatum, white petrolatum, purified lanolin, liquid paraffin), animals and plants oil and combination thereof. In particular preferred is a combination of beeswax and petrolatum. In addition to the base described above, the ointment of the present invention may optionally comprise paraffin such as liquid paraffin, lanolin, animals and plants oil, natural wax, hydrogenated soybean phospholipid (lecitin), higher alcohol. Preferably, the ointment base of the present invention is immiscible in triacetin.

The base of a plaster includes for example polymers such as acrylic acid ester copolymer, silicone resin, polyisobutylene resin, styrene-isoprene-styrene block copolymer, styrene-butadiene-styrene block copolymer. The plaster further comprises for example tackifiers such as rosin, rosin ester or petroleum resin, plasticizers such as polybutene, olive oil, liquid paraffin or liquid isoprene, or fillers such as titanium oxide, zinc oxide or silica.

The base of a cataplasm includes for example glycerin, water, polyacrylate, sodium polyacrylate, methylvinylether-maleic anhydride copolymer, carboxy vinyl polymer, gum arabic, alginic acid, methyl cellulose, hydroxypropylcellulose, gelatin. The cataplasm may further comprise for example wetting agents such as propylene glycol or sorbitol, fillers such as kaolin, titanium oxide or talc, or absorbents such as crotamiton or diisopropyl adipate.

The base of a cream includes for example hydrocarbone such as white petrolatum, wax, liquid paraffin or squalane, higher alcohol such as cetanol, stearyl alcohol or behenyl alcohol, fatty acid esters such as medium-chain triglyceride, isopropyl myristate or diisopropyl adipate, polymers such as carboxy vinyl polymer, hydroxypropylcellulose, polyvinyl pyrrolidone or sodium hyaluronate, or polyol such as glycerin, propylene glycol, 1,3-butylene glycol. The cream may further comprises for example surfactants such as polyoxyethyleneglycol fatty acid ester or polyoxyethyleneglycol fatty acid ester glycol alkyl ether, pH regulators such as diisopropanolamine or sodium hydrate, stabilizers such as sodium hydrogenphosphate, sodium chloride or sodium sulfite, preservatives such as methylparaben or propylparaben, or absorbent such as crotamiton or menthol.

Beeswax is a member of natural wax, including white beeswax. Preferably, beeswax is column-purified beeswax in which impurities such as pigment, peroxide or the like are excluded (for example, Beeswax-S (Croda Japan K.K.)). Preferably, the ointment of the present invention may comprise beeswax at 1.0 to 10% by weight, more preferably 2 to 9% by weight, still more preferably 4 to 8% by weight, most preferably 5 to 7% by weight for the total amount of the ointment.

Petrolatum includes normal petrolatum such as white petrolatum or yellow petrolatum, preferably column-purified petrolatum in which impurities such as pigment, peroxide or the like are excluded (for example, Crolatum V (Croda Japan K.K.)). Preferably, the ointment of the present invention may comprise petrolatum at 60 to 99% by weight, more preferably 70 to 95% by weight, most preferably 80 to 90% by weight for the total amount of the ointment.

The external preparation of the present invention may comprise commonly used additives, such as emulsifying agent, wetting agent, stabilizing agent, stabilizer, dispersant, plasticizer, pH regulator, absorbent, gelator, preservative, filler, preserving agent, antiseptic, pigment, flavoring agent, freshener, thickener, antioxidant, skin-lightening agent, ultraviolet absorber. It is also possible to add trace amount of, for example less than 1% by weight for total amount of the preparation of surfactant such as Tween® 20, 80 or the like. Actual additives to be added in the preparation and its purpose can be easily understood by a person skilled in the art. It is also understood that a certain compound may exert two or more properties.

Preferably, the wetting agent includes, but not limited to, for example glycerin, propyleneglycol, dipropyleneglycol, sodium hyaluronate, cholesterol, pullulan or the like.

Preferably, the stabilizing agent or the stabilizer includes, but not limited to, for example edetic acid (EDTA), citric acid, sodium citrate, L-arginine, tocopherol, silicone, polyoxyethylene sorbitan fatty acid ester or the like.

Preferably, the freshener includes, but not limited to, for example camphor, menthol, plant extract flavor or the like.

Preferably, thickener includes, but not limited to, for example gum arabic, guar gum, carrageenan, carboxyvinyl polymer, cellulose, polyacrylate or the like.

In another embodiment, the present invention relates to a method for preparing an external preparation comprising tacrolimus, which method comprising a step of solubilizing tacrolimus in triacetin. In more particular embodiment, the method for preparing an external preparation comprising tacrolimus comprises following steps:
(1) solubilizing tacrolimus in triacetin; and
(2) mixing the triacetin solution of tacrolimus with a base. Each of additives or a mixture of any additives is independently added to the base, triacetin, the triacetin solution of tacrolimus or the mixture of the solution and the base before or during the step (1) or before, during or after the step (2).

The step (1) above is preferably carried out at 60° C. to 80° C. with any conventional agitator, for example magnetic stirrer (Yazawa Kagaku: KF-800), homogenizer (IKA Japan: T-25), vacuum emulsification agitator (Mizuho Kogyo: PVQ-1 to 5), vacuum emulsifier (Primix: T.K. AGI HOMO MIXER 2M-03 to 5 types) or the like. There may be a risk that tacrolimus would not rapidly solubilize with triacetin at less than 60° C. There also may be a risk that tacrolimus would be decomposed or triacetin would evaporate at more than 80° C. Therefore such conditions are not preferred. The step (2) above is preferably carried out by dispersing at 60 to 80° C., for example about 70° C. for an appropriate time period with any of said conventional agitators, cooling gradually with stirring and by finalizing stirring when the mixture reaches 20 to 40° C., for example 30 to 40° C., preferably about 35° C.

The ointment of the present invention can be prepared for example by using any conventional method for preparing an ointment, for example according to the method described in Examples below. For example, the ointment of the present invention may be prepared as following: heating an oleaginous base to melt, mixing and semicooling the base; solubilizing tacrolimus in a small amount of triacetin; dispersing tacrolimus-solubilized triacetin into the base; mixing until homogeneous dispersion is obtained (Liquefaction Method).

Thus obtained external preparation of the present invention has low dermal or mucosal irritation and high stability. The dermal or mucosal irritation may be determined by for example any known animal testing or dermal or mucosal test model, for example by the dermal irritation test described in Examples below. The stability may be determined by for example any known stability testing, for example by the stability test described in Examples below.

The external preparation of the present invention is useful for treating cutaneous diseases, for example inflammatory or autoimmune cutaneous diseases, especially contact dermatitis, atopic dermatitis, eczematous dermatitis such as medication-related eczematous dermatitis, photo-eczematous eruption or primary irritation dermatitis, urticaria, erythema, psoriasis, lichen planus, pemphigus, pemphigoid or eczematous dermatitis in particular atopic dermatitis. The subject to be treated by the external preparation of the present invention includes, but not limited to, warm-blooded animals including human, for example dog, cat, bovine, hog, horse, sheep, goat, monkey, rabbit, rat or mouse.

The dose and dosage of the external preparation of the present invention can be readily determined on the basis of conditions to be treated, formulation, administration route, age and body weight of the subject, sex or general health and the base or the like. Preferably, tacrolimus is administered at 0.1 to 500 mg/day, preferably 1 to 100 mg/day, more preferably 5 to 10 mg/day once or more a day, for example 1 to 6 times a day.

EXAMPLES

Example 1

Preparation Example 1

Into triacetin 4.0 g, tacrolimus 0.1 g was dissolved at 60° C. to 80° C. with heating (Solution I). Beeswax 1.0 g and petrolatum 94.9 g were melted and mixed, followed by adding said Solution I and stirring with magnetic stirrer (Yazawa Kagaku: KF-800) and homogenizer (IKA Japan: T-25). Stirring was continued under water-cooling until the mixture reaches 40° C. to provide tacrolimus 0.10 ointment (Example).

In addition, propylene carbonate was used as substitute for triacetin to provide another ointment (Reference).

TABLE 1

| Formulation (g) | Example | Reference |
| --- | --- | --- |
| Tacrolimus | 0.1 | 0.1 |
| Triacetin | 4.0 | — |
| Propylene carbonate | — | 4.0 |
| Beeswax | 1 | 1 |
| Petrolatum | q.s. | q.s. |
| Total | 100 | 100 |

Stability Test

The Example and Reference ointments were stored at 3° C. or 30° C. for one week. Thereafter, each ointment 10 g (10 mg as tacrolimus) was added to a mixture of acetonitrile 5 mL and hexane 20 mL and mixed with stirring. The solvent was removed, to acetonitrile layer hexane 20 mL was further added and mixed with stirring. The acetonitrile layer was collected and subjected to high-performance liquid chromatography under the following conditions to determine the amount of tautomers (decomposed product of tacrolimus) and other related substances.

TABLE 2

Test Condition

| | |
| --- | --- |
| Detector | Ultraviolet absorptiometer (Wavelength: 210 nm) |
| Column | Stainless tube with 4.6 mm in internal diameter, 15 cm in length, filled with octylsilanized silica gel for liquid chromatography (particle size 5 μm) |
| Column Temperature | About 60° C., constant |
| Mobile Phase A | Trifluoroacetic acid (1 -> 10000) |
| Mobile Phase B | Acetonitrile |
| Gradient (vol %) | 0 to 40 minutes: Mobile Phase A 60 -> 44, Mobile Phase B 40 -> 56<br>40 to 41 minutes: Mobile Phase A 44 -> 60, Mobile Phase B 56 -> 40<br>41 to 45 minutes: Mobile Phase A 60, Mobile Phase B 40 |
| Flow Rate | 2.0 mL/minutes |

The results of the stability test are as shown in the table below.

TABLE 3

| | Storage Condition | Tautomers (I + II) (%) | Other related substances (%) | Total related substances (%) |
| --- | --- | --- | --- | --- |
| Example | 30° C. | 3.30 | 2.58 | 5.88 |
| | 3° C. | 2.79 | 2.57 | 5.36 |
| Reference | 30° C. | 4.14 | 2.88 | 7.02 |
| | 3° C. | 5.25 | 3.34 | 8.59 |

The ointment of the present invention comprising triacetin is stable for tacrolimus comparing with the Reference comprising propylene carbonate.

Dermal Irritation Test

Primary Rabbit Skin Irritation Test

Rabbits (Japanese White, Male, Body weight 2.0 kg or more) were dehaired in their back with electric clipper on the day before applications. 0.5 g of the preparation of Example 1 or 0.5 g of the same preparation but excluding the active ingredient was applied with a patch test plaster for animals (Torii Yakuhin K.K.) with lint (2.5×2.5 cm) lined with parafilm. For the purpose of avoiding from falling away the plaster, a collar is placed for 24 hours. One group comprises 5 animals.

After 24 hours from the application, the collar and the plaster were removed and then application sites were cleaned with absorbent cotton. After 24, 48 and 72 hours from the application, erythema and crust formation or edema formation were scored according to the cutaneous reactions evaluation criteria of Draize method.

TABLE 4

Cutaneous reactions evaluation criteria (Draize)

1) Erythema and crust formation

0: No erythema
1: Slightest erythema (slightly observable)
2: Evident erythema
3: Moderate to severe erythema
4: Deep-red severe erythema with mild crust formation (deep lesion)

2) Edema formation

0: No edema
1: Slightest edema (slightly observable)
2: Evident edema (clearly distinguishable)
3: Moderate edema (about 1 mm of swelling)
4: Severe edema (more than 1 mm of swelling and expands over the application cite)

The sum of the scores of erythema/crust formation and edema formation at the application site at 24 and 72 hours after the application was divided by 4 to determine the individual irritation indices. The indices were averaged to determine primary irritation indices (P.I.I.). The degrees of irritation were sectioned from P.I.I. according to irritation sections of Draize to evaluate the irritation against rabbit skin.

TABLE 5

Irritation sections (Draize)
Primary irritation indices (P.I.I.)

| | |
| --- | --- |
| 0 | No irritation |
| 2 or less | Mild irritation |
| more than 2, less than 6 | Moderate irritation |
| 6 or more | Severe irritation |

No erythema/crust formation and edema formation was observed in each cases for the whole period of the observation. In both cases P.I.I. were 0, so they were sectioned to "No irritation".

Preparation Example 2

Tacrolimus hydrate 1.02 g is dissolved to triacetin 5 g with heating, and macrogol 400 (83.98 g) and macrogol 4000 (10 g) are added thereto. The mixture is further mixed with heating, thereafter cooled to provide non-aqueous gel.

TABLE 6

Non-aqueous gel (water soluble gel)

| Definition | Formulation | Content (%) |
| --- | --- | --- |
| Active ingredient | Tacrolimus hydrate | 1.02 |
| Solubilizer | Triacetin | 5 |

TABLE 6-continued

Non-aqueous gel (water soluble gel)

| Definition | Formulation | Content (%) |
|---|---|---|
| Base | Macrogol 4000 | 10 |
| Base | Macrogol 400 | q.s. |
| | Total | 100 |

(% means % by weight, herein and hereinafter)

Preparation Example 3

Tacrolimus hydrate 1.02 g is dissolved to triacetin 5 g with heating, and glyceryl tri 2-ethylhexanoate is added. The solution is added to liquid paraffin 83.98 g and dispersed with a stirrer. Further dextrin palmitate 5 g is added thereto with stirring to turn into a gel to provide an emulsion lyogel.

TABLE 7

Emulsion lyogel (oily gel)

| Definition | Formulation | Content (%) |
|---|---|---|
| Active ingredient | Tacrolimus hydrate | 1.02 |
| Solubilizer | Triacetin | 5 |
| Base | Glyceryl tri 2-ethylhexanoate | 5 |
| Base | Liquid paraffin | q.s. |
| Gelator | Dextrin palmitate | 5 |
| | Total | 100 |

Preparation Example 4

Methylparaben 0.15 g and propylparaben 0.1 g are dissolved to purified water with heating, and after cooling to 40° C. or less, concentrated glycerin 10 g, citric acid 0.5 g and Carbopol 980 (0.5 g) are dissolved. Tacrolimus hydrate 1.02 g is dissolved to triacetin 20 g with heating, and added to the solution and dispersed with a stirrer. Aqueous solution of sodium hydrate is added dropwise with stirring to adjust pH to pH 4 to 7 to form a gel. Purified water is added to adjust the total amount to 100 g to provide an aqueous gel. Still, a lotion can be prepared upon using Carbopol 980 at 0.1 g to 0.2 g.

TABLE 8

Aqueous gel

| Definition | Formulation | Content (%) |
|---|---|---|
| Active ingredient | Tacrolimus hydrate | 1.02 |
| Solubilizer | Triacetin | 20 |
| Base | Purified water | q.s. |
| Gelator | Polyacrylic acid (Carbopol 980) | 0.5 |
| pH regulator | NaOH | q.s. |
| pH regulator | Citric acid | 0.5 |

TABLE 8-continued

Aqueous gel

| Definition | Formulation | Content (%) |
|---|---|---|
| Wetting agent | Conc. glycerin | 10 |
| Preservative | Methylparaben | 0.15 |
| Preservative | Propylparaben | 0.1 |
| | Total | 100 |

Preparation Example 5

Triacetin 20 g, cetanol 3 g, stearyl alcohol 3 g and Tween 80 (0.5 g) are mixed at 70° C. and tacrolimus hydrate 1.02 g is added thereto and dissolved with heating. To the solution, methylparaben 0.15 g and propylparaben 0.1 g dissolved in purified water 52.23 g is added and mixed with a stirrer. The solution is cooled with stirring to provide a cream.

TABLE 9

Emulsion ointment: cream (o/w)

| Definition | Formulation | Content (%) |
|---|---|---|
| Active ingredient | Tacrolimus hydrate | 1.02 |
| Solubilizer | Triacetin | 20 |
| Base | Cetanol | 3 |
| Base | Stearyl alcohol | 3 |
| Emulsifier | Tween 80 | 0.5 |
| Base | Purified water | q.s. |
| Preservative | Methylparaben | 0.15 |
| Preservative | Propylparaben | 0.1 |
| | Total | 100 |

What is claimed is:

1. An external preparation in an ointment form comprising tacrolimus, triacetin and a base in which tacrolimus-solubilizing triacetin droplets are dispersed in the base.

2. The external preparation according to claim 1, wherein the percentage of the amount of tacrolimus to triacetin is from 0.03 to 30% by weight.

3. The external preparation according to claim 1 comprising a mixture of beeswax and petrolatum as an ointment base.

4. The external preparation according to claim 3, wherein the beeswax is column-purified beeswax.

5. The external preparation according to claim 3, wherein the petrolatum is column-purified petrolatum.

6. A method for preparing an external preparation comprising tacrolimus, comprising a step of solubilizing tacrolimus with triacetin.

7. The external preparation according to claim 2 comprising a mixture of beeswax and petrolatum as an ointment base.

8. The external preparation according to claim 7, wherein the beeswax is column-purified beeswax.

9. The external preparation according to claim 7, wherein the petrolatum is column-purified petrolatum.

* * * * *